US006554825B1

United States Patent
Murray et al.

(10) Patent No.: US 6,554,825 B1
(45) Date of Patent: Apr. 29, 2003

(54) VARIABLE PULSE DURATION, ADJUSTABLE WAVELENGTH MEDICAL LASER SYSTEM

(75) Inventors: Steven C. Murray, Santa Cruz, CA (US); Scott A. Davenport, Half Moon Bay, CA (US); Tony D. Coleman, San Jose, CA (US)

(73) Assignee: Laserscope, San Jose, CA (US)

( * ) Notice: Subject to any disclaimer, the term of this patent is extended or adjusted under 35 U.S.C. 154(b) by 0 days.

(21) Appl. No.: 09/569,595

(22) Filed: May 9, 2000

(51) Int. Cl.[7] .............................................. A61B 18/20
(52) U.S. Cl. .............................. 606/11; 606/10; 606/13
(58) Field of Search ....................................... 606/9–12

(56) References Cited

U.S. PATENT DOCUMENTS

| | | | |
|---|---|---|---|
| 4,829,262 A | 5/1989 | Furumoto | 330/4.3 |
| 4,872,177 A * | 10/1989 | Baer et al. | 372/108 |
| 4,907,235 A | 3/1990 | Kuizenga | 372/21 |
| 4,977,571 A | 12/1990 | Furumoto et al. | 372/54 |
| 5,025,446 A | 6/1991 | Kuizenga | 372/21 |
| 5,066,291 A * | 11/1991 | Stewart | 359/326 |
| 5,066,293 A | 11/1991 | Furumoto | 606/9 |
| 5,130,997 A * | 7/1992 | Ortiz et al. | 372/103 |
| 5,144,630 A * | 9/1992 | Lin | 359/330 |
| 5,151,909 A | 9/1992 | Davenport et al. | 372/22 |
| 5,260,953 A * | 11/1993 | Rowe | 372/105 |
| 5,287,380 A | 2/1994 | Hsia | 372/69 |
| 5,307,358 A * | 4/1994 | Scheps | 372/100 |
| 5,363,388 A * | 11/1994 | Shi et al. | 359/329 |
| 5,457,707 A * | 10/1995 | Sobey et al. | 359/330 |
| 5,598,426 A | 1/1997 | Hsia et al. | 372/53 |
| 5,624,435 A | 4/1997 | Furumoto et al. | 606/10 |
| 5,668,824 A | 9/1997 | Furumoto et al. | 372/54 |
| 5,720,772 A | 2/1998 | Eckhouse | |
| 5,754,573 A * | 5/1998 | Yarborough et al. | 372/22 |
| 5,795,153 A * | 8/1998 | Rechmann | 433/215 |
| 5,841,800 A | 11/1998 | Davenport et al. | 372/22 |
| 5,911,718 A * | 6/1999 | Yarborough et al. | 606/6 |
| 6,038,240 A * | 3/2000 | Deutsch et al. | 372/10 |
| 6,080,148 A * | 6/2000 | Damasco et al. | 606/10 |
| 6,156,030 A * | 12/2000 | Neev | 216/94 |
| 6,157,661 A * | 12/2000 | Walker et al. | 372/38.02 |

* cited by examiner

*Primary Examiner*—Linda C. M. Dvorak
*Assistant Examiner*—H M Johnson
(74) *Attorney, Agent, or Firm*—Mark A. Haynes; Haynes Beffel & Wolfeld LLP

(57) ABSTRACT

A medical laser system is disclosed for generating a pulsed output beam of variable pulse duration and wavelength. The on time of the laser is the pulse duration which is generated by a Q-switch operated in a repetitive mode as a train of micropulses. According to one embodiment, a repetitively Q-switched frequency-doubled solid state laser produces an input beam which is subsequently used to excite a dye laser. An excitation source of the solid state laser is modulated to control the pulse duration of the input beam. The dye laser receives the input beam and responsively generates an output beam of adjustable wavelength having a pulse duration corresponding to the pulse duration of the input beam. The wavelength of the output beam is controlled by adjusting a tuning element of the dye laser. The dye laser is coupleable to a delivery system for directing the output laser beam to a biological tissue target. By carefully controlling the pulse duration and wavelength of the beam delivered to the target tissue, a user of the laser system may avoid or minimize damage to tissue adjacent to the target tissue.

27 Claims, 3 Drawing Sheets

VARIABLE PULSE DURATION, ADJUSTABLE WAVELENGTH MEDICAL LASER SYSTEM

FIELD OF THE INVENTION

The present invention relates generally to lasers, and more particularly to dye lasers suitable for medical therapies such as selective photothermolysis and photodynamic therapy.

DESCRIPTION OF THE PRIOR ART

Many medical procedures employing lasers require relatively long pulse durations at specific wavelengths to achieve optimal results. Therapies such as laser removal of hair and vascular and pigmented lesions rely upon the selective photothermolysis of blood vesicles and/or cells. The principles of selective photothermolysis were first described by Anderson and Parrish in "Selective Photothermolysis: Precise Microsurgery by Selective Absorption of Pulse Radiation", *Science*, Vol. 220, pp. 524–27 (1983).

To provide selective photothermolysis in an efficient manner, the following three criteria must be satisfied:

(1) The target tissue must absorb more of the incident laser light than the adjacent tissue;

(2) The intensity of the laser light and the absorption of the target tissue must be sufficiently high to coagulate, kill, or vaporize the target tissue, and;

(3) The pulse duration of the laser light must be short enough to avoid or minimize overheating of adjacent tissue due to thermal diffusion from the target tissue, but long enough to prevent explosive boiling of the target and/or adjacent tissue.

The foregoing criteria are generally satisfied by matching the laser pulse duration and wavelength to the thermal and spectral characteristics of the target tissue. In order to accommodate targets of varying size and absorption coefficients, it is necessary to adjust pulse duration and wavelength over a fairly wide range.

To date, prior art lasers used or intended for use in selective photothermolysis and similar procedures have fallen into one of two categories: fixed pulse duration, variable wavelength lasers, and fixed wavelength, variable pulse duration lasers. The former category includes long pulse flashlamp pumped dye lasers (known as FLPDLs), various examples of which are disclosed in U.S. Pat. Nos. 5,066,293; 5,287,380; 5,624,435, and; 5,668,824. FLPDLs designed for medical use have maximum pulse durations of approximately 1.5 milliseconds, which limits their use to very small blood vessels. Another problem associated with FLPDLs is that while they allow adjustment of the output beam wavelength, they do not offer the ability to adjust the pulse duration over a clinically relevant range.

Examples of lasers in the second category (fixed wavelength, variable pulse duration lasers) include "Star Pulsed" KTP lasers available from Laserscope, Inc. of San Jose, Calif. These lasers employ a pulsed arc lamp to generate high intensity light having a wavelength of 532 nanometers and pulse durations ranging from 1–100 ms. Variable duration pulse 532 nanometer light can also be generated using flashlamp-pumped lasers, such as the Versipulse laser available from Coherent Laser of Santa Clara, Calif. Although the pulse durations of these lasers render them suitable for treating medium- and large-sized blood vessels, the wavelength of the output beam of lasers of the foregoing description cannot be adjusted to match the spectral characteristics of the target tissue.

In view of the limitations of prior art lasers, there is a need for a medical laser system that offers the ability to adjust both pulse duration and wavelength in order to match thermal and spectral characteristics of the target tissue and thereby achieve highly efficient and effective results.

SUMMARY

The present invention provides a medical laser system having an output beam that can be adjusted over a clinically relevant range of pulse durations and wavelengths.

According to one embodiment, the medical laser system includes a solid state laser for generating an input beam of adjustable pulse duration. The solid state laser includes a laser medium, such as a neodymium: yttrium aluminum garnet (Nd:YAG) rod, which is pumped by an excitation source typically comprising an arc lamp. Light emitted by the laser medium is passed through an acousto-optic Q-switch and a frequency doubling non-linear crystal. Power supplied to the excitation source is modulated to produce pulses of a specified duration, each pulse comprising a train of repetitively Q-switched micropulses.

The input beam is coupled to a dye laser, either directly or through an optical fiber. The dye laser generates an output beam of adjustable wavelength having a pulse duration corresponding to the pulse duration of the input beam. The dye laser includes a dye cell onto which the input beam is focussed, and a tuning element, such as a birefringent filter. Adjustment of output beam wavelength is accomplished by changing the dye composition and/or varying the filter orientation. A portion of the output beam may be split off and diverted to power and wavelength detectors, which provide feedback signals to a control processor driving the excitation source, Q-switch and tuning element. A conventional delivery system, which may comprise an optical fiber and associated focussing optics, is coupleable to the dye laser and serves to direct the output beam onto a biological tissue target.

In accordance with certain embodiments of the medical laser system, the wavelength of the output beam produced by the dye laser may be varied between 550 nanometers and 750 nanometers, and the pulse duration varied between 0.1 and 900 milliseconds. A clinician operating the laser may thus adjust the beam characteristics in order to achieve optimal selective photothermolysis of the target tissue. The medical laser may also be advantageously used for a variety of other therapies and procedures, including hair removal, drug activation in photodynamic therapy (PDT), and cutting and/or drilling tissue.

DETAILED DESCRIPTION OF PREFERRED EMBODIMENTS

Figure 1:
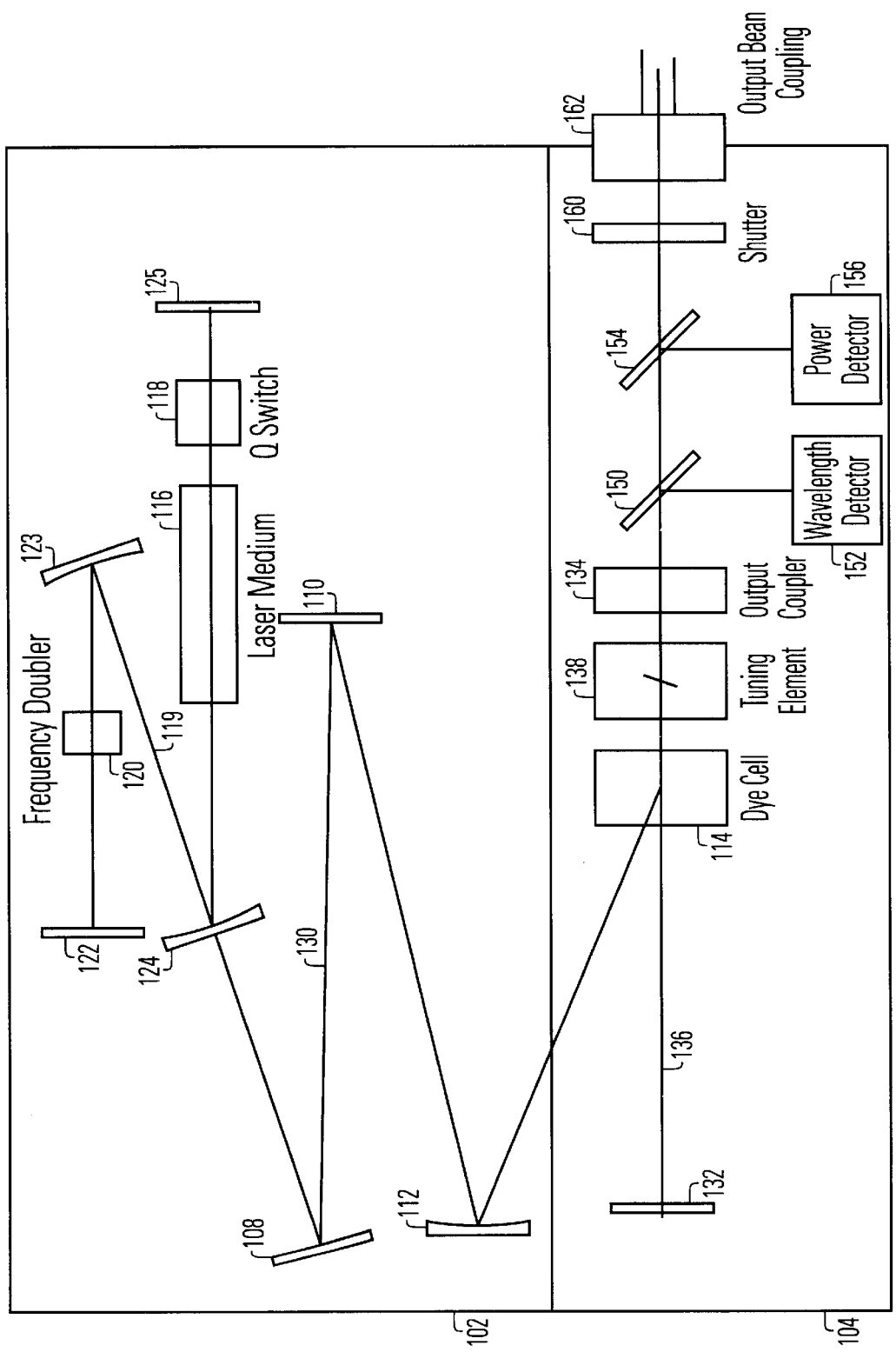
FIG. 1 is a schematic of a medical laser system showing a frequency-doubled, repetitively Q-switched solid state laser coupled to a dye laser.

FIG. 1 is a schematic of a medical laser system 100 in accordance with one embodiment of the invention. Medical laser 100 generally includes a frequency doubled solid state laser 102 for generating an input laser beam of variable pulse duration, and a dye laser 104 for receiving the input beam and responsively emitting an output laser beam of variable wavelength having a pulse duration substantially equal to the pulse duration of the input beam. A conventional delivery system (not depicted), coupled to dye laser 104, directs the output beam to a biological tissue target. In the embodiment depicted in FIG. 1, solid state laser 102 and dye laser 104 are disposed within a common housing, and are optically coupled by mirrors 108, 110 and 112, which direct and focus the input beam generated by solid state laser 102 onto dye cell 114. As will be discussed below in connection with FIG. 4, other embodiments of the medical laser system may utilize a solid state laser and a dye laser which are physically separate and are optically coupled by an optical fiber or similar expedient.

Figure 2:
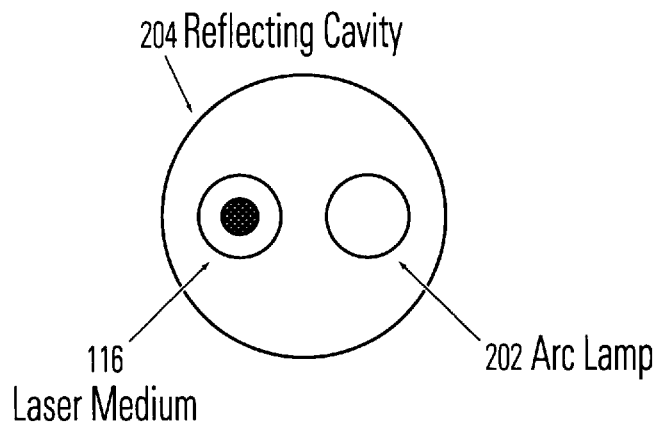
FIG. 2 is a cross-sectional view of a lamp housing, arc lamp and laser medium.

Solid state laser 102 includes a laser medium 116, Q-switch 118, and frequency doubler 120 positioned along an optical path 119 defined by end mirror 122, turning mirror 123, output coupler 124 and end mirror 125. Laser medium 116 preferably comprises an elongated member or rod of Nd:YAG material, but may alternatively comprise any suitable material wherein transition metal ions (such as chromium, titanium, and lathanide) are disposed within a crystalline host (such as YAG, yttrium lithium fluoride (YLF), sapphire, alexandrite, spinel or YAP). As depicted in FIG. 2, laser medium 116 is positioned proximal to an excitation source preferably comprising a krypton arc lamp 202, which pumps laser medium 116 to cause it to begin emitting light. Laser medium 116 and arc lamp 202 are, preferably arranged in mutually parallel relation within lamp housing 204, although other geometries and configurations known in the art may be employed. Lamp housing 204 may be adapted with liquid coolant channels that communicate with a coolant recirculation pump in order to prevent overheating of arc lamp 202 and laser medium 116. Those skilled in the art will recognize that other excitation sources, such as flashlamps or laser diodes, may be substituted for arc lamp 202. As will be described below in further detail in connection with FIGS. 3 and 4, arc lamp 202 is modulated by varying the amount of energy supplied thereto in order to adjust a pulse duration of the input beam generated by solid state laser 102.

Frequency doubler 120 preferably comprises a nonlinear crystal such as a KTP or LBO crystal. The frequency doubler is operative to double the frequency of laser light generated by laser medium 116. In accordance with one embodiment of medical laser system 100, a Nd:YAG laser medium 116 emits infrared light having a wavelength of 1064 nanometers which is frequency doubled by a non-linear crystal frequency doubler 120 to produce green light having a wavelength of 532 nanometers. The green light travels along optical path 119 and is extracted by output coupler 124 to supply an input beam to dye laser 104 along path 130. Although FIG. 1 depicts frequency doubler 120 as being located within the resonator cavity defined by end mirrors 122 and 125, frequency doubler 120 may alternatively be located in beam path 130 exterior to the resonator cavity.

End mirrors 122 and 125 and turning mirror 123 are highly reflective (>99.5%) at both the 532 nanometer (green light) and 1064 nanometer (infrared light) wavelengths, whereas output coupler 124 is highly reflective at the 1064 nanometer wavelength and transmissive at the 532 nanometer wavelength. In the preferred embodiment depicted in FIG. 1, end mirrors 122 and 125 are flat, and turning mirror 123 and output coupler 124 are provided with concave reflecting surfaces which cause the beam at the output of laser medium 116 to be relay imaged onto frequency doubler 120.

The resonator design of solid state laser 102 is described in further detail in U.S. Pat. No. 4,907,235 ("Intra-cavity Beam Relay for Optical Harmonic Generation" to Kuizenga) and in U.S. Pat. No. 5,151,909 ("Frequency Doubled Laser Having Programmable Pump Power Modes and Method for Controllable Lasers" to Davenport et al.), both of which are incorporated by reference.

Q-switch 118 is preferably of the acousto-optic type, but may alternatively comprise a mechanical device such as a rotating prism or aperture, or an electro-optical device. In a preferred embodiment of solid state laser 102, Q-switch 118 is operated in a repetitive mode to cause a train of micropulses to be generated. The micropulse repetition rate may typically be varied in the range of 1–100 kilohertz. As will be discussed below, the duration of each train of micropulses, collectively deemed a pulse, is governed by the duration of operation of arc lamp 202.

Frequency doubled light extracted by output coupler 124 is thereafter directed along path 130 defined by turning mirrors 108, 110 and 112, which are highly reflective at the 532 nanometer wavelength. In the embodiment depicted in FIG. 1, turning mirrors 108 and 110 are flat, wherein mirror 112 has a concave reflecting surface to focus the beam onto dye cell 114 of dye laser 104.

Dye laser 104 includes an end mirror 132 and a dye output coupler 134 defining an optical path 136 in which are located dye cell 114 and a tuning element 138. Dye cell 114 may comprise conventional laterally opposed sapphire, YAG, quartz or glass windows defining a volume through which a dye solution is continually pumped at high speed and excited by the input beam, causing the dye solution to fluoresce and emit light. Conversion efficiencies in preferred embodiments of laser system 100 are typically about 30–50 percent (in contradistinction to flashlamp-pumped dye lasers, which typically exhibit conversion efficiencies on the order of <5 percent). A variety of dye solutions which may be used in dye laser 104, including (without limitation) R6G, Rhodamine 590, Rhodamine 575, and Sulfa Rhodmine 660.

As in conventional dye lasers, tuning element 138 may be provided to tune the laser output within the gain curve of the selected dye solution. Tuning element 138 is generally capable of reducing the bandwidth of the beam to <2 nanometers, and is used to match the output beam to the spectral characteristics of the target tissue. For example, in one embodiment of laser system 100, the wavelength of the output beam may be varied between 570 and 620 nanometers, although different and wider ranges are achievable, depending on the dye solution selected and the performance of other system components. Tuning element 138 may preferably comprise a birefringent filter having a rotational orientation controlled by an associated stepper motor. Alternatively, tuning element 138 may comprise an etaloh, prism, filter, or other suitable device.

Dye output coupler 134 is configured to reflect a portion of the beam incident thereon along path 136, and to transmit the remainder to produce an output beam. Depending on system requirements, the percentage of the beam reflected by dye output coupler will vary between 10 and 95 percent.

Beam splitter 150 is disposed in the path of the output beam and is configured to direct a small portion of the beam onto wavelength detector 152 and to transmit the remainder of the beam. Similarly, beam splitter 154 directs a small portion of the output beam onto power detector 156 and transmits the remainder. Wavelength detector 152 and power detector 156 are of conventional design and are operative to generate output signals representative of, respectively, the wavelength and power of the output beam for use in a control feedback loop.

An automatically or manually actuated shutter 160 is operable to selectively block the output beam when emission of the output beam from laser system 100 is undesirable. A conventional fiber coupling 162 is utilized to couple laser system 100 to a delivery system (not depicted) capable of directing the output beam onto the tissue target. The delivery system, examples of which are well known in the art and hence need not be discussed in detail herein, generally comprises an optical fiber or articulated arm extending between a proximal end received by and removably secured to fiber coupling 162, and a distal end secured to a handpiece (such as the DermaStat™ handpiece available from Laserscope, Inc.) or scanner for focusing or scanning the output beam onto the target.

Figure 3:
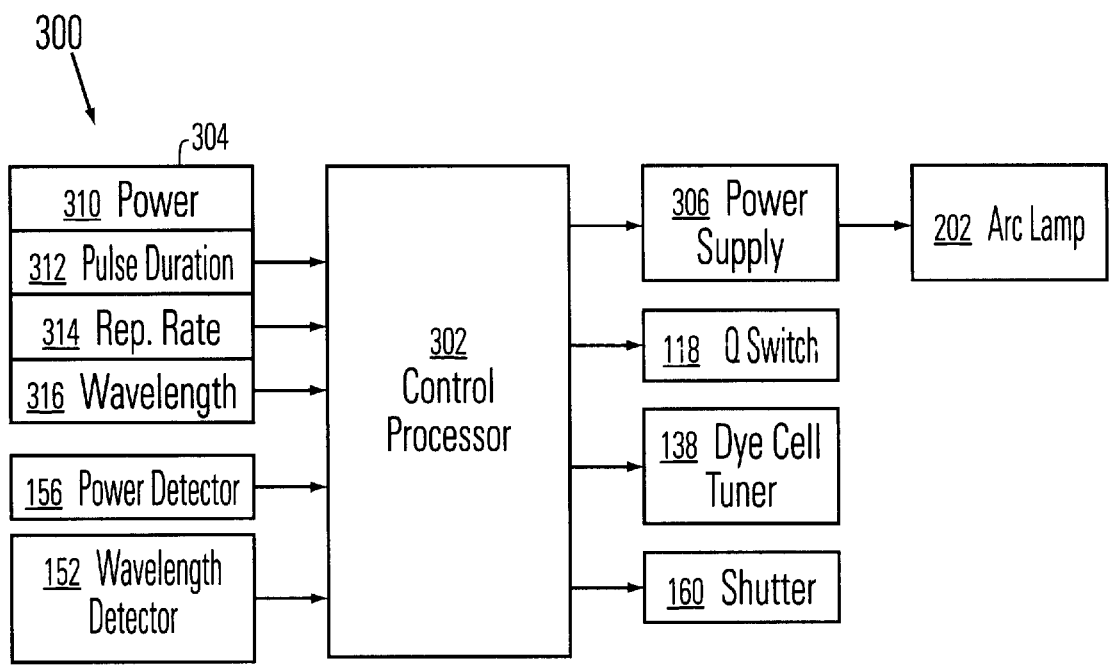
FIG. 3 is a schematic of a control system for controlling and monitoring the operation of the medical laser system.

FIG. 3 is a block diagram of a control system 300 for controlling and operating laser system 100. Control system 300 includes a control processor 302 which receives input from a variety of sources including user controls 304, power detector 156 and wavelength detector 152. User controls 304 are provided to allow the user to control and adjust various aspects of the operation of laser system 100 so as to achieve optimal results for a given therapeutic procedure. User controls 304 may include, for example, a power or fluence control 310, pulse duration control 312, repetition rate control 314, and wavelength control 316. In one embodiment of laser system 100, user controls 304 are adjusted via through an alphanumeric user interface.

Control processor 302 is configured to process input received from user controls 304 and detectors and to accordingly generate output signals for adjusting characteristics of the output beam to match the user inputted values. Control processor 302 may comprise, for example, a general-purpose processor which executes control software embodying a set of algorithms specifying input-output relationships. In particular, control processor 302 generates and transmits output signals to power supply 306, Q-switch 118 (or alternatively, a driver which supplies power to Q-switch 118), dye cell tuning element 138, and shutter 160. The output signal delivered to power supply 306 modulates the energy supplied to arc lamp 202, which in turn controls the average power and pulse durations of the input and output beams. The output signal delivered to Q-switch 118 controls the repetition rate of the component micropulses. The output signal delivered to tuning element 138 controls positioning or other operational characteristics to thereby adjust the wavelength of the output beam emitted by dye laser 104. Finally, the output signal delivered to shutter 160 controls its actuation to selectively block the output beam path when emission of the beam from medical laser system 100 is undesirable.

Figure 4:
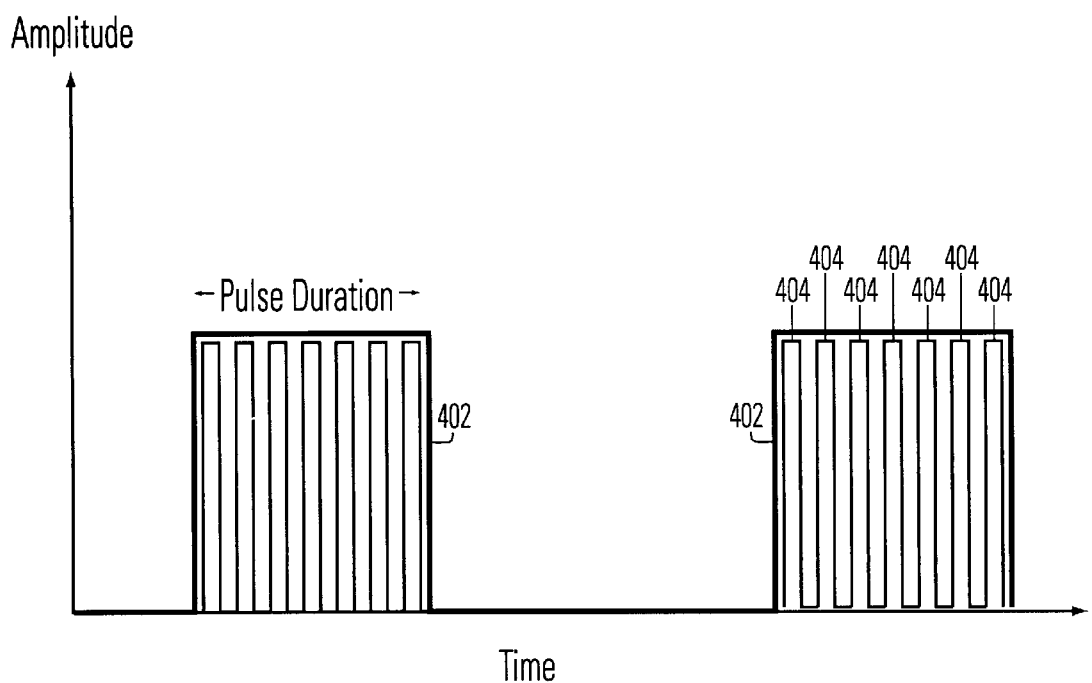
FIG. 4 is a graph depicting the structure of an output beam pulse.

FIG. 4 is a graph depicting the amplitude of the output beam emitted by medical laser system 100 as a function of time. As discussed above, laser beam pulses 402 are each defined by trains of Q-switched micropulses 404. While a relatively small number of micropulses 404 are depicted for purposes of clarity, an actual pulse 402 may comprise hundreds or thousands of component micropulses 404. Each pulse 402 may contain up to 30 joules of energy. The pulse duration of pulses 402, which is adjusted by modulating the operation of arc lamp 202, may typically be varied in the range of 0.1 to 200 milliseconds, although pulse durations as high as 900 milliseconds may be achieved using laser system 100.

Figure 5:
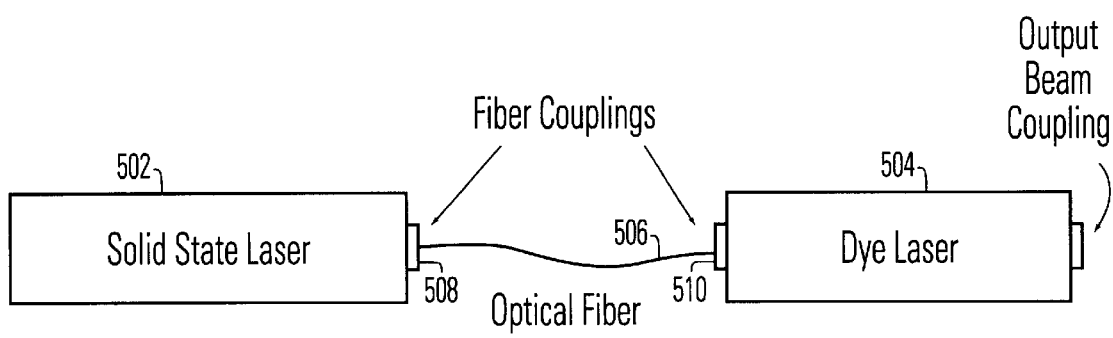
FIG. 5 is a block diagram of a second embodiment of the invention, wherein the solid state laser is coupled to the dye laser via an optical fiber.

FIG. 5 depicts a medical laser system 500 in accordance with an alternative embodiment of the invention. In contradistinction to laser system 100, solid state laser 502 and dye laser 504 are housed separately and are optically coupled by an optical fiber 506 (rather than by turning mirrors 108, 110 and 112 of the FIG. 1 embodiment), which directs a frequency doubled, variable pulse duration input beam generated by solid state laser 502 onto a dye cell located within dye laser 504. The proximal and distal ends of optical fiber 506 are received within and removably secured to fiber couplings 508 and 510, which are provided, respectively, at solid state. In all other respects, solid state laser 502 and dye laser 504 are substantially identical to solid state laser 102 and dye laser 104, as described above.

Those skilled in the art will recognize that by adjusting the wavelength and pulse duration of the output beam to appropriate values, medical laser system 100 may be effectively employed in connection with a variety of therapies and procedures. These therapies and procedures include, but are not limited to, removal of cutaneous and internal vascular lesions; hemostasis of bleeding ulcers; suppression of choroidal neovascularization leading to blindness; tattoo removal; hair removal; removal of arterial plaque; and, photodynamic therapy (PDT) for treatment of various tumors.

While the invention has been particularly shown and described with reference to preferred embodiments thereof, it will be understood by those skilled in the art that various changes in form and details may be made therein without departing from the spirit and scope of the invention, as defined by the appended claims.

What is claimed is:

1. A variable pulse duration, adjustable wavelength medical laser system, comprising:
   a solid-state laser for generating an input laser beam, including:
      a solid-state laser medium;
      an excitation source for pumping the laser medium, the excitation source being modulated to control pulse duration of the input laser beam; and
      a frequency doubler, disposed in a path of the input laser beam, for doubling the frequency of the input laser beam;
   a dye laser, for receiving the frequency-doubled input laser beam and for responsively generating an output laser beam of adjustable wavelength, the output laser beam having a pulse duration corresponding to the pulse duration of the frequency-doubled input beam; an output beam coupler, for optically coupling output beam to a delivery system configured to direct the output laser beam onto a biological tissue target; and
   a controller, coupled to the solid-state laser and the dye laser, including a user input device, adapted to adjust the pulse duration and the adjustable wavelength in response to user input specifying a pulse duration within a clinically relevant range of pulse durations and a wavelength within a clinically relevant range of wavelengths for a plurality of medical purposes.

2. The medical laser system of claim 1, wherein the solid state laser is repetitively Q-switched to generate a train of micropulses, each train of micropulses collectively representing a pulse.

3. The medical laser system of claim 1, wherein the clinically relevant range of pulse duration is about 0.1 to about 900 milliseconds.

4. The medical laser system of claim 1, wherein the clinically relevant range of wavelength of the output beam is a bout 550 nanometers to about 750 nanometers.

5. The medical laser system of claim 1, wherein the solid-state laser includes a resonator and the frequency doubler is positioned internal to the resonator of the solid-state laser.

6. The medical laser system of claim 1, wherein the solid-state laser includes a resonator and the frequency doubler is positioned external to the resonator of the solid-state laser.

7. The medical laser system of claim 1, further comprising a pulse duration controller for modulating the excitation source.

8. The medical laser system of claim 1, wherein the excitation source comprises a flashlamp.

9. The medical laser system of claim 1, wherein the excitation source comprises an arc lamp.

10. The medical laser system of claim 1, wherein the excitation source comprises a laser diode.

11. The medical laser system of claim 1, wherein the dye laser comprises a tuning element for adjusting the wavelength of the output laser beam.

12. The medical laser system of claim 11, wherein the tuning element comprises a birefringent filter.

13. The medical laser system of claim 1, wherein the laser medium comprises a neodymium-doped yttrium aluminum garnet (Nd:YAG) crystal.

14. The medical laser system of claim 13, wherein the wavelength of the frequency doubled input laser beam is 532 nanometers.

15. The medical laser system of claim 1, further comprising an optical fiber for directing the frequency-doubled input laser beam onto the dye laser.

16. A method for irradiating biological tissue, comprising the steps of:
   accepting user input specifying a pulse duration within a clinically relevant range of pulse durations and specifying a wavelength within a clinically relevant range of wavelengths for a plurality of medical purposes;
   using an excitation source, exciting a solid-state laser medium to generate a laser beam;
   modulating the excitation source to adjust a pulse duration of the laser beam in response to said user input;
   disposing a frequency doubler in a path of the laser beam to generate a frequency-doubled input laser beam;
   receiving the frequency-doubled input laser beam at a dye laser and responsively generating a wavelength-altered output laser beam having a pulse duration corresponding to the pulse duration of the input beam;
   adjusting a wavelength of the output laser beam in response to said user input; and
   directing the output laser beam onto a biological tissue target.

17. The method of claim 16 further comprising a step of repetitively Q-switching the input laser beam to form a train of micropulses, each train collectively representing a pulse.

18. The method of claim 16 wherein the biological tissue target comprises a vascular lesion.

19. The method of claim 16 wherein the biological tissue target comprises ocular tissue.

20. The method of claim 16 wherein the biological tissue target comprises a tumor.

21. The method of claim 16, wherein the clinically relevant range of pulse duration is about 0.1 to about 900 milliseconds.

22. The method of claim 16, wherein the clinically relevant range of wavelength is about 550 nanometers to about 750 nanometers.

23. The method of claim 16, wherein the step of directing the output laser beam onto a biological tissue target comprises directing the laser be am along an optical fiber.

24. The method of claim 16, wherein the biological tissue target comprises human hair.

25. The method of claim 17, wherein the train of micropulses have a frequency in the range of 0.5 to 100 kilohertz (kHz).

26. The method of claim 16 wherein the biological tissue target comprises arterial plaque.

27. The method of claim 16, wherein said plurality of medical purposes includes at least two of removal of cutaneous and internal vascular lesions, hemostasis of bleeding ulcers, suppression of choroidal neovascularization leading to blindness, tattoo removal, hair removal, removal of arterial plaque, and photodynamic therapy for treatment of various tumors.

* * * * *